US007419798B2

(12) United States Patent
Ericson

(10) Patent No.: US 7,419,798 B2
(45) Date of Patent: Sep. 2, 2008

(54) RAPID AND SENSITIVE DETECTION OF BACTERIA IN BLOOD PRODUCTS, URINE, AND OTHER FLUIDS

(75) Inventor: Daniel G. Ericson, Rochester, MN (US)

(73) Assignee: Zybac LLC, Rochester, MN (US)

( * ) Notice: Subject to any disclaimer, the term of this patent is extended or adjusted under 35 U.S.C. 154(b) by 84 days.

(21) Appl. No.: 10/968,203

(22) Filed: Oct. 19, 2004

(65) Prior Publication Data

US 2006/0084127 A1   Apr. 20, 2006

(51) Int. Cl.
*C12Q 1/04* (2006.01)
(52) U.S. Cl. ........................................ 435/34
(58) Field of Classification Search .................. None
See application file for complete search history.

(56) References Cited

U.S. PATENT DOCUMENTS

| 3,745,090 | A | 7/1973 | Chappelle |
| 3,933,592 | A | 1/1976 | Clendenning |
| 4,283,490 | A | 8/1981 | Plakas |
| 4,385,113 | A | 5/1983 | Chappelle |
| 4,704,355 | A | 11/1987 | Bernstein |
| 5,258,285 | A | 11/1993 | Aegidius |
| 5,624,810 | A | 4/1997 | Miller |
| 5,736,351 | A | 4/1998 | Miller |
| 6,332,049 | B1 | 12/2001 | Dasgupta |
| 6,395,504 | B1 | 5/2002 | Trudil |
| 6,613,579 | B2 | 9/2003 | Wolcott |
| 6,617,105 | B1 | 9/2003 | Rudi |
| 6,716,391 | B1 | 4/2004 | Olson |
| 2002/0019062 | A1* | 2/2002 | Lea et al. ................. 436/518 |
| 2003/0153028 | A1* | 8/2003 | Refseth et al. ............ 435/34 |

FOREIGN PATENT DOCUMENTS

EP   0126 019 A   11/1984

OTHER PUBLICATIONS

Mitchell et al, "Approaches to the Detection of Bacterial Contamination in Cellular Blood Products," (Transfusion Medicine Reviews), vol. 13, No. 2, Apr. 1999, pp. 132-144.*
Stanley et al, A Review of Bioluminescent ATP Techniques in Rapid Microbiology, (Journal of Bioluminescence and Chemiluminescence), vol. 4, 1989, pp. 375-380.*
Nilsson, LE et al., 1989, Bioluminescent assay of bacterial ATP for rapid detection . . . , J. Bioluminescence Chemiluminescence 3:101-104.
Ruokonen, A et al., 1982, Screening of bacteria in urine using luciferin-luciferase assay . . . , Ann. Clin. Biochem. 19:416-420.
Stanley, PE, 1989, A review of bioluminescent ATP techniques in rapid microbiology, J. Bioluminescence Chemiluminescence 4:375-380.
Lemasters, JJ et al., 1979, Continuous measurement of adenosine triphosphate with firefly luciferase . . . , Meth. Enzymol. 56:530-544.
Higashi, T et al., 1985, Quantitative and continuous analysis of ATP release from blood platelets . . . , Thrombosis Haemostasis 53:65-69.
http://www.genpoint.com/Files/bugsnbeads.html, date accessed: Jan. 21, 2005.
Brecher, ME et al., 1994, Platelet bacterial contamination and the use of a chemiluminescence-linked . . . , Transfusion 34(9):750-755.
Chaney, R et al., 1999, Direct detection of bacteria in cellular blood products using bacterial . . . , Transfusion Medicine 9:177-188.
Gastrin, B et al., 1989, Evaluation of a bioluminescence assay for the detection of bacteriuria, Scand. J. Infect. Dis. 21:409-414.
Hanna, BA, 1986, Detection of bacteriurea by bioluminscence, Methods in Enzymology 133:22-27.
Lundin, A et al., 1989, Bacteriuria testing by the ATP method as an integral part in the . . . , J. Bioluminescence Chemiluminescence 4:381-389.
Lundin, A et al., 1975, Comarison of methods for extraction of bacterial adenine nulceotides . . . , Appl. Microbiol. 30(5):713-721.
Mitchell, K-M. T., et al., 1999, Approaches to the detection of bacterial contamination . . . , Transfusion Medicine Reviews 13(2):132-144.
Molin, O et al., 1983, Rapid detection of bacterial growth in blood cultures by bioluminescent assay . . . , J. Clin. Microbiol. 18:521-525.
"Issue Summary, Blood Products Advisory Committee, Jul. 23, 2004, Update: Experience with Monitoring of Bacterial Contamination of Platelets" published by the U.S. Food and Drug Administration on Jul. 23, 2004, and available on their website at http://www.fda.gov/ohrms/dockets/ac/04/briefing/2004-4057b1_04.pdf.

* cited by examiner

*Primary Examiner*—Jon P Weber
*Assistant Examiner*—Amanda P Wood
(74) *Attorney, Agent, or Firm*—Hugh McTavish

(57) ABSTRACT

The invention provides methods of detecting bacteria in fluids, including blood, platelets and other blood products for transfusion, and urine. The methods are based on lysing the bacteria to release ATP and detecting the ATP. Eukaryotic cell contamination is a problem to be overcome, because eukaryotic cell contain large amounts of ATP. Thus, some of the methods involve separating intact eukaryotic cells (e.g., platelets) from intact bacterial cells before lysing the bacterial cells to release ATP, contacting the ATP with an ATP-consuming enzyme that catalyzes a reaction, and monitoring the enzyme-catalyzed reaction. Typically, the enzyme is luciferin, and the reaction is monitored by detecting light produced by the luciferin. Other methods of the invention involve contacting a fluid sample with a support surface that binds bacterial cells, lysing the bacterial cells to release ATP, contacting the ATP with an ATP-consuming enzyme, and monitoring the enzyme-catalyzed reaction. Apparatuses for carrying out the methods are also disclosed.

25 Claims, 6 Drawing Sheets

RAPID AND SENSITIVE DETECTION OF BACTERIA IN BLOOD PRODUCTS, URINE, AND OTHER FLUIDS

BACKGROUND

Over nine million platelet units are transfused in the United States every year. The platelets are stored at room temperature to prevent loss of function and thus are particularly susceptible to bacterial contamination. Platelets are often given to cancer chemotherapy patients to treat platelet depletion and the resulting anemia and risk of bleeding caused by chemotherapy. These patients are also immunocompromised and thus at particular risk from bacterial contamination of the platelets. The number of cases of illnesses and death due to contaminated platelets has only recently been gathered.

Bacterial contamination has been the leading cause of transfusion-related deaths over the past three years (1). Bacterial contamination levels as low as $10^2$ to $10^3$ CFU/ml have been associated with fever and positive blood culture. Studies at Johns Hopkins and Dana-Farber revealed rates of sepsis following platelet transfusion from 0.005% to 0.14%, depending on the site and whether the platelets were derived from random donors or single donor apheresis. In the 33,829 transfusions documented, a total of nine cases of sepsis were found (2, 3). The rate of sepsis appears to be lower than the rate of bacterial contamination in studies of platelet purity. It has been widely suggested that the rate of sepsis from platelet transfusion is underreported for a variety of clinical and regulatory reasons.

Because of the risk of sepsis, the FDA requires platelets to be discarded after five days of storage. For a short period (1984-1986) the FDA permitted platelet storage for seven days, reversing the regulation after data on bacterial proliferation proved troublesome (4).

The available means for testing for bacteria in platelets are too slow, not sensitive enough, or too cumbersome. One method is culturing the growth of microorganisms from the platelets, such as the BACT/ALERT system. However, this requires culturing for one to three days (5). Another method is gram staining of a sample of platelet concentrate for visual microscopic identification of bacteria. But this requires significant labor and was only sensitive to $10^6$ colony forming units (CFU) per ml (5). Acridine orange staining and fluorescence microscopy improved the sensitivity to $10^4$-$10^5$ CFU/ml (5). Visual observation of platelet swirling, or assaying for pH or glucose concentration changes have also been used, but these are not sufficiently sensitive or reliable (5).

A PCR method was used to detect *Yersinia enterocolitica*. This method was quite sensitive, but took six hours and was specific for only one species (5).

Fluorescent antibodies have also been used to detect bacteria with flow cytometry (5). That has the potential to be sensitive, but is expensive, fairly time consuming, and is only detects the species recognized by the antibodies.

A method of detecting bacteria using detection of labeled oligonucleotides that hybridize to bacterial rRNA (6). But the process took four hours.

Bacteria have been detected by luminescence detection of bacterial ATP (7, U.S. Pat. No. 3,933,592). Bacteria are lysed to release their ATP, and the ATP is detected by reaction with luciferase and luciferin to produce light. However, eukaryotic cells have far more ATP than bacterial cells, so even a small contamination with eukaryotic cells gives unreliable results. In one method, blood cells were lysed with TRITON X-100, the debris was separated from bacteria by density gradient centrifugation, and the bacterial cell layer of the gradient was extracted, treated to lyse any bacteria, and assayed for ATP by the luciferin-luciferase assay (8).

New methods to detect bacteria in platelets are needed. Preferably, the methods would be inexpensive, fast, detect bacteria of any clinically significant species, and be sensitive, i.e., detect very low numbers of bacteria. New methods of detecting bacteria in other fluids are also needed. These fluids include whole blood for transfusion, whole blood taken from a patient for diagnosis of sepsis, bone marrow stem cells for a bone marrow transplant, serum, plasma, and urine. Rapid detection of bacteria in urine is needed for diagnostic purposes in both human and veterinary medicine.

SUMMARY

The invention provides methods to detect bacteria in platelet concentrate, other blood products for transfusion, blood from a patient assayed for diagnostic purposes, urine, and other fluids. Apparatuses to carry out the methods are also provided. The methods can detect and quantify bacteria in fluids in less than five minutes, allowing detection of bacteria in blood or urine at the bedside or during a clinical visit, and allowing detection of bacteria in platelets or other blood products immediately before they are to be transfused into a patient. The methods are also very sensitive, allowing detection of, in some cases, less than 100 bacterial cells per ml of fluid sample. The methods are not species specific and can be used to quantify any bacteria.

One of the major problems with detecting bacteria in fluids by ATP detection is that most fluids also contain somatic cells or other eukaryotic cells (including platelets), which have large quantities of ATP, masking the smaller amounts of ATP found in bacteria. Some of the methods of the invention involve separating intact eukaryotic cells (including platelets) from intact bacteria prior to lysing the bacteria, to solve the problem of contamination with ATP from the eukaryotic cells. This is done by filtering out the eukaryotic cells with a filter that allows bacterial cells to pass through, or by binding the bacterial cells to a surface that selectively binds bacterial cells and does not bind eukaryotic cells. The binding surface can also serve to concentrate the bacterial cells, increasing the sensitivity of their detection. Alternatively, if a filtration step is used to remove intact eukaryotic cells, the bacterial cells can be concentrated by a second filtration step with a filter that captures the bacteria.

Other methods of the invention involve contacting a fluid sample suspected to contain bacteria with a support surface that binds the bacteria, where the contacting step is not necessarily used to separate the bacteria from intact eukaryotic cells. For instance, the eukaryotic cells could be first selectively lysed in the sample, and then the sample contacted with the bacteria-binding surface to concentrate the bacteria and/or remove them from debris and from non-bacterial ATP.

Thus, one embodiment of the invention provides a method of detecting bateria in a fluid sample suspected of containing bacteria that involves: (a) separating intact eukaryotic cells from intact bacterial cells that may be present in the fluid sample; (b) lysing the bacterial cells to release bacterial ATP into a fluid to generate a bacterial lysate fluid; (c) contacting the bacterial ATP in the bacterial lysate fluid with an ATP-consuming enzyme that catalyzes a reaction in an ATP assay fluid; and (d) monitoring the enzyme-catalyzed reaction in the ATP assay fluid.

Another embodiment of the invention provides a method of detecting bacteria in a fluid sample suspected of containing bacteria that involves: (a) contacting the fluid sample with a support surface that binds bacterial cells to concentrate the bacterial cells and/or separate the bacterial cells from other components in the fluid sample; (b) lysing the bacterial cells to release bacterial ATP into a fluid to generate a bacterial lysate fluid; (c) contacting the bacterial ATP in the bacterial lysate fluid with an ATP-consuming enzyme that catalyzes a reaction in an ATP assay fluid; and (d) monitoring the enzyme-catalyzed reaction in the ATP assay fluid.

Another embodiment of the invention provides a system for detecting bacteria in a fluid sample that includes: (a) a holding means for receiving a device for separating intact eukaryotic cells from intact bacterial cells in a fluid sample; (b) a fluid-tight material forming an assay chamber adapted to receive fluid flow from the device for separating intact eukaryotic cells from intact bacterial cells in a fluid sample; and (c) a light detector functionally linked to the assay chamber to detect light emitted in the assay chamber.

Another embodiment of the invention provides a system for detecting bacteria in a fluid sample that includes: (a) a holding means for receiving a support surface that binds intact bacterial cells in a fluid sample; (b) a fluid-tight material forming an assay chamber adapted to receive fluid flow from the support surface that binds intact bacterial cells in a fluid sample; and (c) a light detector functionally linked to the assay chamber to detect light emitted in the assay chamber.

DETAILED DESCRIPTION

Figure 1:
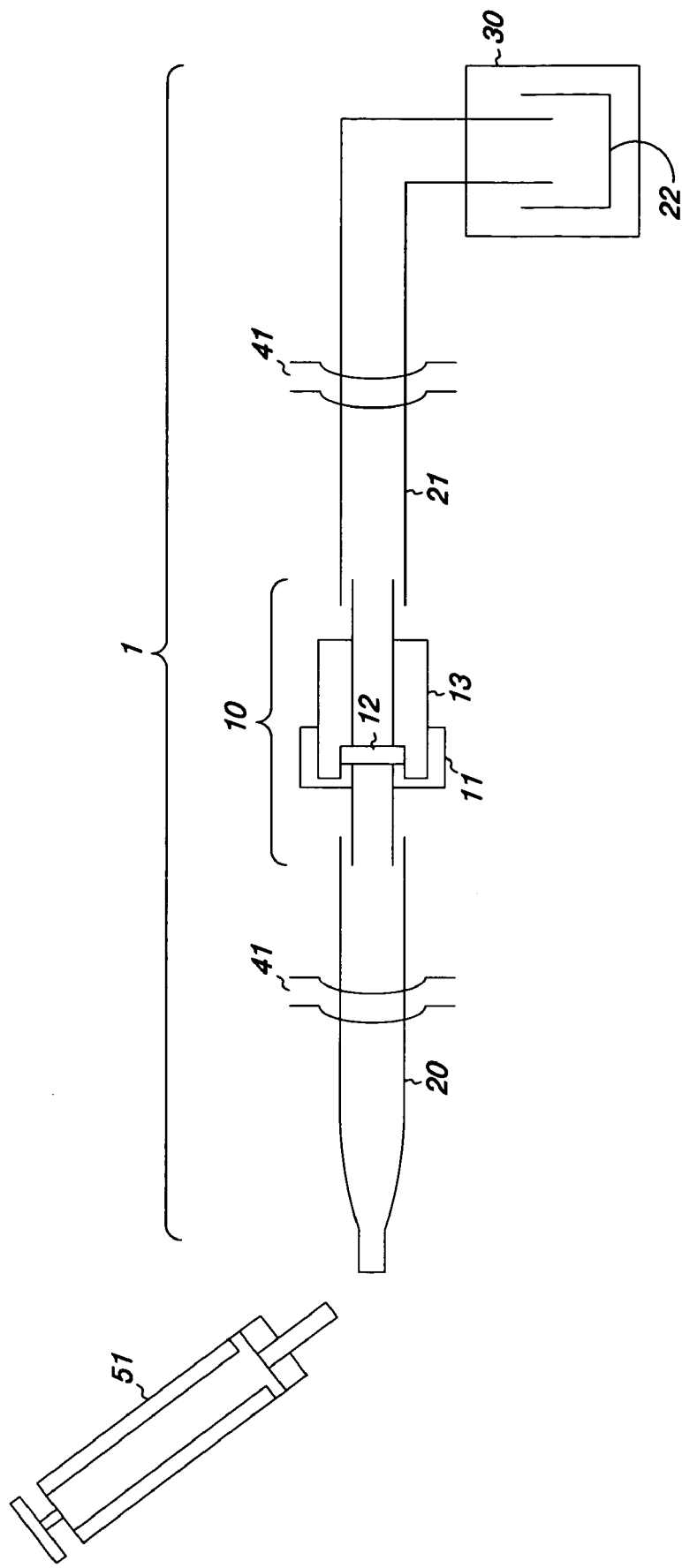
FIG. 1 shows a system of the invention for detecting bacteria in fluids.

Definitions:

The term "eukaryotic cell," as used herein, includes nucleated cells and naturally occurring membrane-enclosed ATP-containing bodies of eukaryotic origin without nuclei, such as platelets, that are suspected to be contained in a fluid.

A "filter," as used herein, is a membrane or device that allows differential passage of particles and molecules based on size. Typically this is accomplished by having pores in the filter of a particular nominal size. For instance, filters of particular interest in this invention have pores sufficiently large to allow passage of bacteria but small enough to prevent passage of platelets or other eukaryotic cells present in the fluid sample of interest. Bacteria are typically smaller than 1 micron in diameter; platelets are approximately 3 microns in diameter; and nucleated eukaryotic cells are typically 10-200 microns in diameter.

The term "platelet concentrate" as used herein refers to a blood fraction enriched in platelets to be used for transfusion into a mammal for the purpose of giving the mammal platelets.

Reference to a support surface that "binds bacteria" means that under the conditions of the contacting, the support surface binds a sufficient fraction of the bacteria present in the fluid to allow detection of the bacteria. Typically, this is at least 50% or at least 90% of the bacteria present in the fluid.

Reference to a support surface that "does not bind eukaryotic cells" means that under the conditions of the contacting used, the binding of eukaryotic cells suspected of being present in the fluid is low enough that the cells are sufficiently removed to not interfere with detection of bacteria that bind to the surface. Typically, under the conditions of the contacting, the support surface binds less than 10%, more preferably less than 1%, more preferably less than 0.1%, of the eukaryotic cells present in the fluid, and most preferably binds an undetectable number of eukaryotic cells.

Reference to a support surface that "does not bind ATP" means that under the conditions of the contacting used, the binding of ATP present in the fluid prior to lysing the bacteria is low enough that the amount of ATP bound does not interfere with detection of bacteria that bind to the surface. Typically, under the conditions of the contacting, the support surface binds less than 10%, more preferably less than 1%, more preferably less than 0.1%, of the ATP present in the fluid, and most preferably binds an undetectable amount of ATP.

Description:

Some embodiments of the invention involve separating intact eukaryotic cells (e.g., platelets) from intact bacterial cells before lysing the bacterial cells to release ATP, contacting the ATP with an ATP-consuming enzyme that catalyzes a reaction, and monitoring the enzyme-catalyzed reaction.

The bacteria are lysed to release bacterial ATP into a fluid to generate a bacterial lysate fluid, and the bacterial ATP in the bacterial lysate fluid is contacted with an ATP-consuming enzyme that catalyzes a reaction in an ATP assay fluid. In some embodiments, the enzyme is present and able to act in the fluid in which the bacteria are released, so that the bacterial lysate fluid and the ATP assay fluid are the same fluid. In some embodiments, other necessary cofactors such as luciferin are added to the bacterial lysate fluid to allow the enzyme reaction to proceed and form the ATP assay fluid. In some embodiments, the bacterial lysate fluid is contacted with immobilized ATP-consuming enzyme to form the ATP assay fluid. In some embodiments, the bacterial lysate fluid is mixed with a separate fluid containing the ATP-consuming enzyme to form the ATP assay fluid.

In some embodiments, the intact eukaryotic cells include platelets.

In some embodiments, the step of separating intact eukaryotic cells from bacterial cells includes filtering the eukaryotic cells using a filter that blocks the eukaryotic cells and allows the bacterial cells to pass through, to generate a filtered fluid sample containing the bacterial cells.

In some embodiments, the step of separating the intact eukaryotic cells from bacterial cells includes contacting the fluid sample with a support surface that binds the bacterial cells and does not bind the eukaryotic cells.

The support surface typically binds all or almost all types of bacteria. In some embodiments, the support surface binds most species of bacteria. In some embodiments, the support surface binds at least five genera of bacteria. In some embodiments, the support surface binds all of the following species of bacteria: *Bacilus cereus, Bacillus substilis, Clostridium perfringens, Corynebacterium* species, *Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans*.

Support surfaces that bind bacteria without binding platelets or other eukaryotic cells include surfaces consisting of or containing polycations (e.g., polyethyleneimine or polylysine). Polycations nonspecifically bind the outer surface, i.e., the outer membrane or cell wall, of all or nearly all species of bacteria. Beads that bind bacteria without binding eukaryotic cells including platelets are commercially available from GenPoint (Oslo, Norway). GenPoint BUG TRAP C-version in particular is reported to bind *Acinetobacter, Alcaligenes, Bacillus, Boretella, Borrelia, Chlamydia, Clostridium, Corynebacterium, E. coli, Enterobacter, Haemophilus, Helicobacter, Klebsiella, Listeria, Micrococcus, Mycobacterium, Neisseria, Propionebacterium, Proteus, Pseudomonas, Salmonella, Serratia, Streptococcus, Staphylococcus*, and *Yersinia*.

Binding surfaces that can be used to concentrate bacteria but that also bind platelets or other eukaryotic cells include glass, polyacrylic acid, fibronectin, laminin, collagen, Arg-Gly-Asp oligopeptide, or Phe-His-Arg-Arg-Ile-Lys-Ala (SEQ ID NO:1) oligopeptide. All of those surfaces also nonspecifically bind the outer surface, i.e., the outer membrane or cell wall, of all or nearly all species of bacteria.

In one embodiment, the support surface does not contain an antibody.

In one embodiment, the support surface comprises a plurality of antibodies recognizing a plurality of genera of bacteria. In one embodiment, the support surface comprises a plurality of antibodies that collectively recognize *Bacilus cereus, Bacillus substilis, Clostridium perfringens, Corynebacterium* species, *Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans*.

In one embodiment of the methods of the invention, the method involves, after the step of filtering the eukaryotic cells, contacting the filtered fluid sample with a support surface that binds bacteria. The support surface in some embodiments does not bind eukaryotic cells. This provides an additional purification step to back up the filtration of eukaryotic cells. However, since the eukaryotic cells are already filtered from the fluid in these embodiments, in some cases the support surface may bind eukaryotic cells as well as bacterial cells without any harm since eukaryotic cells are not expected to be present in the filtered fluid sample.

In some embodiments of the invention involving a support surface that binds bacteria, the support surface does not bind ATP.

In one embodiment, the step of separating intact eukaryotic cells from intact bacterial cells that may be present in the fluid sample involves before the step of contacting the fluid sample with a support surface that binds the bacteria, filtering the eukaryotic cells from the fluid sample using a filter that blocks the eukaryotic cells and allows the bacterial cells to pass through.

In some embodiments, the bacterial cells are lysed while bound to the support surface to release bacterial ATP into a fluid to generate a bacterial lysate fluid. In other embodiments, the bacterial cells are first eluted from the support surface with an elution fluid, before lysing the bacterial cells to release ATP and generate a bacterial lysate fluid. After elution, the bacterial cells could be filtered to concentrate them or bound to another binding surface to concentrate them, before lysing the cells.

In particular embodiments, the volume of the ATP assay fluid is smaller than the volume of the fluid sample. That is, the bacterial cells are concentrated before lysis. This improves the sensitivity of the assay and allows detection of a lower concentration of bacterial cells in the fluid sample.

The bacterial cells can be lysed by various methods. These include heat (e.g., to 100° C. or above) or contact with detergents, or a combination of the two. Other methods include contact with acid or base. Trichloroacetic acid and perchloric acid, and probably other acids, have the advantage of denaturing bacterial apyrase, which otherwise can hydrolyze the released ATP (9, 10). Bacterial cells can also be lysed by sonication, contact with particles (e.g., glass beads), freeze-thaw, organic solvents (e.g., chloroform, phenol, or n-butanol), enzymes (e.g., lysozyme), or french press. Combinations of two or more of the above lysing methods or agents may also be used.

If acid or base is used to lyse the bacterial cells, the pH may need to be adjusted after the lysis step before adding, or simultaneously with adding, luciferase or another ATP-consuming enzyme used in the assay in order for the enzyme to work. Luciferase also requires $Mg^{2+}$ as a cofactor, so this may need to be added. Exposure to $O_2$ is also necessary. The luciferase reaction is shown below, where E is luciferase and $LH_2$ is luciferin.

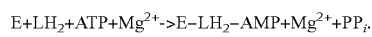

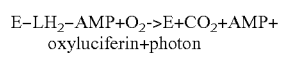
oxyluciferin+photon

The light is detected as an indication of ATP concentration. Provided excess luciferin and luciferase are present, the rate of reaction is proportional to ATP concentration. Because the overall forward reaction is strongly favored, in the absence of significant inhibitors the total light generated, as well as the reaction rate, is proportional to ATP concentration. A correlation between light intensity and ATP concentration has been shown over a 1000-fold range of ATP concentration. The overall reaction can occur very rapidly, with reaction times less than 500 msec demonstrated (16).

Oxyluciferin is a powerful non-competitive inhibitor of the luciferase reaction. With a half-saturation constant of 0.23 μM, even at very low ATP concentrations the buildup of oxyluciferin can result in a rapid decay in luminescence (17).

Some lysis agents, including trichloroacetic acid, may somewhat decrease the light signal from the luciferase reaction. The amount of inhibition can be determined by assays, and in some cases can be reversed by, e.g., for TCA, neutralization of the acid following lysis.

In particular embodiments, the step of monitoring the enzyme-catalyzed reaction involves monitoring a product produced by the reaction.

In preferred embodiments, the product is light.

In preferred embodiments where the product monitored is light, the enzyme is luciferase and the method involves contacting the bacterial ATP with luciferase and luciferin.

In particular embodiments, the fluid sample is a bodily fluid of a mammal, e.g., blood, spinal fluid, urine, or a blood product such as platelet concentrate.

In particular embodiments, the blood product is whole blood, serum, plasma, bone marrow stem cell concentrate, or erythrocyte concentrate.

In one embodiment, the bodily fluid is urine. In another embodiment, the bodily fluid is spinal fluid.

In particular embodiments, the bodily fluid is for transfusion into a mammal.

One of the advantages of the invention is that it gives good sensitivity of detection of bacteria. In particular embodiments, the methods detect at least three bacterial genera at a level of 10,000, 1,000, or 100 bacterial colony forming units (CFU) per ml of the fluid sample, In particular embodiments, the methods detect 10,000 CFU per ml of each of the following species of bacteria: *Bacilus cereus, Bacillus substilis, Clostridium perfringens, Corynebacterium* species, *Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes,* and *Streptococcus viridans.*

In particular embodiments of the filter used to block eukaryotic cells and allow bacterial cells to pass through, the filter has a pore size of 1-10 microns. In particular embodiments, the filter has a pore size of about 1 micron, about 2 microns, 1-3 microns, 1-5 microns, about 5 microns, or about 10 microns.

One embodiment of the invention provides a method of detecting bacteria in a fluid sample suspected of containing bacteria that involves: (a) contacting the fluid sample with a support surface that binds bacterial cells to concentrate the bacterial cells and/or separate the bacterial cells from other components in the fluid sample; (b) lysing the bacterial cells to release bacterial ATP; (c) contacting the bacterial ATP with an ATP-consuming enzyme that catalyzes a reaction; and (d) monitoring the enzyme-catalyzed reaction.

A particular embodiment of that method includes, before the step of contacting the fluid sample with a support surface that binds bacterial cells, selectively lysing eukaryotic cells that may be present in the fluid sample without substantially lysing bacterial cells that may be present in the fluid sample. TRITON-X-100, for instance, at room temperature, neutral pH, and appropriate concentrations, lyses platelets and other somatic cells without lysing bacteria.

Contacting the fluid with a support surface that binds bacterial cells after selectively lysing the eukaryotic cells can separate the bacterial cells from eukaryotic cell enzymes and debris that might interfere with assaying bacterial ATP, provided the relevant eukaryotic cell enzymes and debris do not bind to the bacteria-binding surface. In particular, it is advantageous if the bacteria-binding surface does not bind ATP, since that background ATP can interfere with assay of the ATP released with lysis of the bacterial cells. It can also be advantageous for the bacteria-binding surface to not bind apyrase released from the lysed eukaryotic cells, since apyrase would hydrolyze the bacterial ATP when it is released.

In particular embodiments of the method involving contacting the fluid sample with a support surface that binds bacteria, the method involves before the step of contacting the support surface, filtering intact eukaryotic cells that may be present in the fluid sample from the fluid sample using a filter that blocks the eukaryotic cells and allows the bacterial cells to pass through.

In particular embodiments, the support surface binds bacterial cells and does not bind eukaryotic cells. In other embodiments, it binds both bacterial and eukaryotic cells.

One embodiment of the invention provides a system for detecting bacteria in a fluid sample that includes: (a) a holding means for receiving a device for separating intact eukaryotic cells from intact bacterial cells in a fluid sample; (b) a fluid-tight material forming an assay chamber adapted to receive fluid flow from the device for separating intact eukaryotic cells from intact bacterial cells in a fluid sample; and (c) a light detector functionally linked to the assay chamber to detect light emitted in the assay chamber.

One embodiment of the system is depicted in FIG. 1. The system 1 includes filtering device 10, containing a filter 12 held in place between two interlocking pieces 11 and 13, is used to filter out intact eukaryotic cells, allowing intact bacterial cells to pass through the device. The filter is held in place by attachment to the ends of tubing sections 20 and 21, with clips 41 holding the tubing sections in place. Syringe 51 can be used to project a fluid sample into the system, forcing it through tubing section 20, filter device 10, tubing section 21, and into assay chamber 22. After lysing intact bacterial cells, ATP in the assay chamber is reacted with luciferin and luciferase to produce light. The light is detected by light detector 30. The light detector can be any suitable device that detects light, including a photomultiplier tube or a photodiode.

Other means for holding the device for separating intact eukaryotic cells from intact bacterial cells 10 can include a clip or receptacle or the like that directly holds the device in place.

Figure 2:
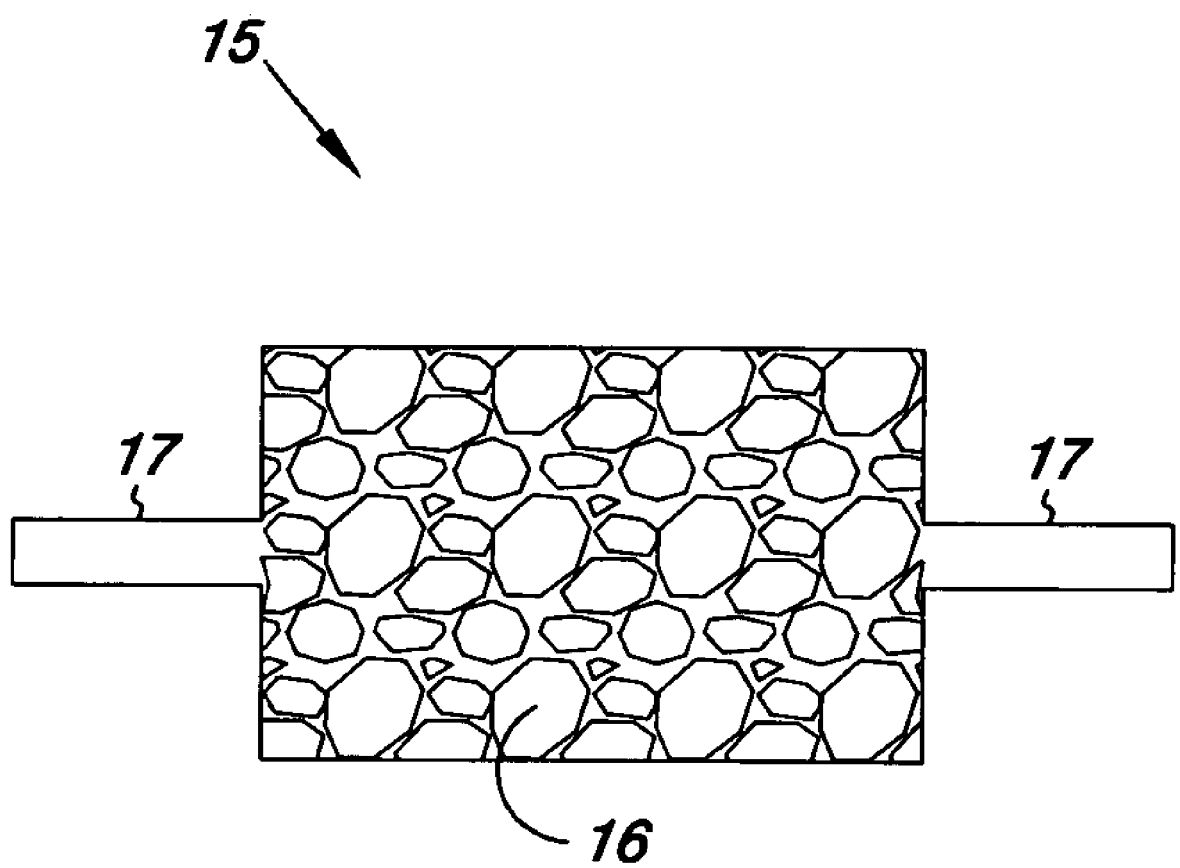
FIG. 2 shows a device for separating intact eukaryotic cells from intact bacterial cells by means of a support surface that binds bacterial cells.

In place of filter device 10, the system can include a device 15 containing a support surface that binds bacteria and does not bind eukaryotic cells. FIG. 2 shows such a device 15, with beads 16 having the bacteria-binding support surface, and ports 17 adapted for engagement with the ends of tubing sections 20 and 21 in FIG. 1. When a fluid sample passes through the device, intact bacterial cells are bound and intact eukaryotic cells pass through and are separated.

In some embodiments, the system includes the device for separating intact eukaryotic cells from intact bacterial cells in the holding means for the device.

Figure 3:
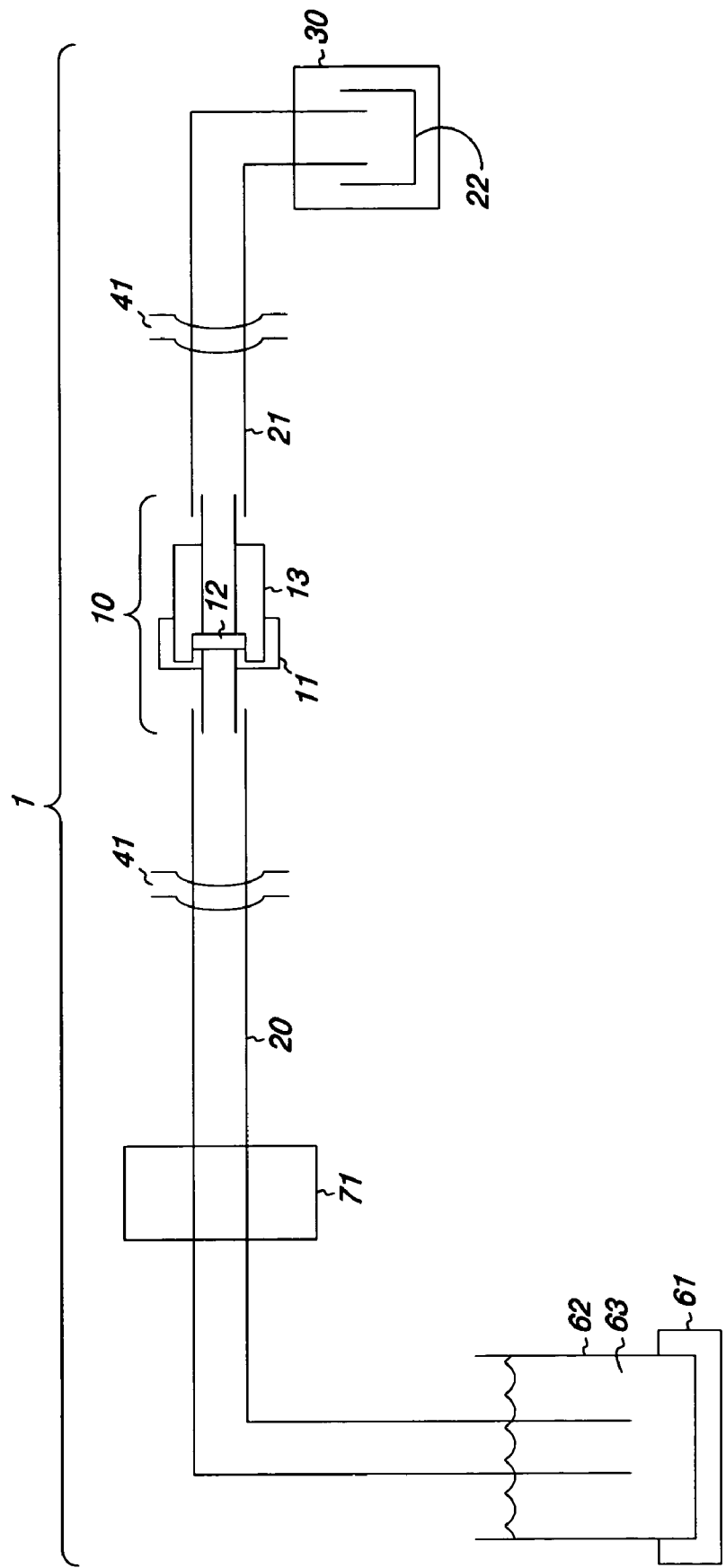
FIG. 3 shows another system of the invention for detecting bacteria in fluids.

In some embodiments of the system, the system includes (d) a holding means for receiving a fluid sample reservoir in fluid communication with the device for separating intact eukaryotic cells from intact bacterial cells; and (e) a pump functionally coupled to the fluid sample reservoir, the device for separating intact eukaryotic cells from intact bacterial cells (separation device), and the assay chamber, to pump fluid from the fluid-sample reservoir to the separation device and from the separation device to the assay chamber. Such a system is shown in FIG. 3. Sample reservoir 62 held on receptacle 61, and holding fluid sample 63 is shown, together with pump 71 for pumping fluid from the sample reservoir to the separation device 10 and the assay chamber 22.

In some embodiments, the assay chamber contains luciferase. For instance, luciferase may be able to be immobilized in the wall of the assay chamber or on beads in the assay chamber. Or luciferase can be added as a solution to the assay chamber.

Figure 4:
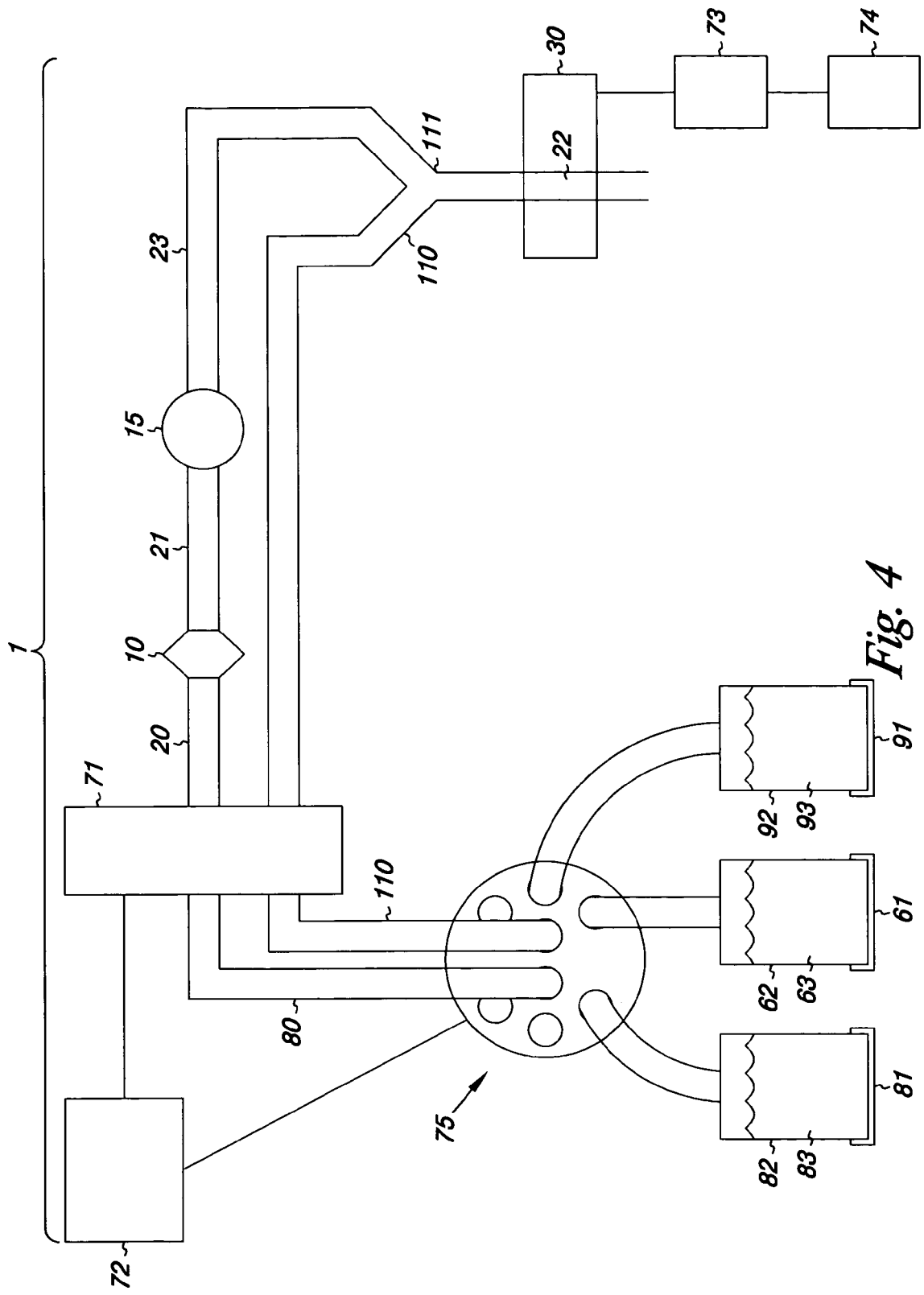
FIG. 4 shows another system of the invention for detecting bacteria in fluids.

FIG. 4 shows several features that are included in some embodiments of the systems of the invention. The system includes a fluid sample reservoir 62 held in a holding means 61 and containing a fluid sample 63 to be assayed for bacteria. The system of FIG. 4 also includes a wash solution reservoir 82 held in a holding means 81 and containing a wash solution 83. A luciferase solution reservoir 92 held by a holding means 9.1 and containing a luciferase solution 93 is also shown. The solutions held in the reservoirs are linked to a multiport selection valve 75, which outputs the appropriate solution pumped by pump 71 to passages 20 or 110. Initially, the fluid sample is pumped through passage 20 to filter device 10, where eukaryotic cells are filtered out, and on to device 15 containing a support surface that binds bacteria. Bacteria in the fluid sample are bound to the support surface. The wash solution 83 is then pumped through passageways 20 and 21 to the bacteria-binding device 15. If the wash solution contains a lysing agent, the wash solution lyses the bacteria bound in device 15, releasing ATP into a bacterial lysate fluid that is carried out into passageway 23.

A luciferase solution 93 can be pumped into passageway 110 with the multiport selection valve and the pump. The multiport selection valve 75 and pump 71 can be controlled by a processor 72. At Y junction 111, the luciferase solution and the bacterial lysate fluid are mixed to form an ATP assay fluid, which is transported into assay chamber 22, which in FIG. 4 is shown as a flow-through cell. Light emitted in the assay chamber is detected by the light detector 30.

A display 74 may be functionally linked to the light detector 30 for displaying raw or processed data from the light detector. In some embodiments, the system contains a processor 73 linked to the detector that processes data from the detector.

Figure 5:
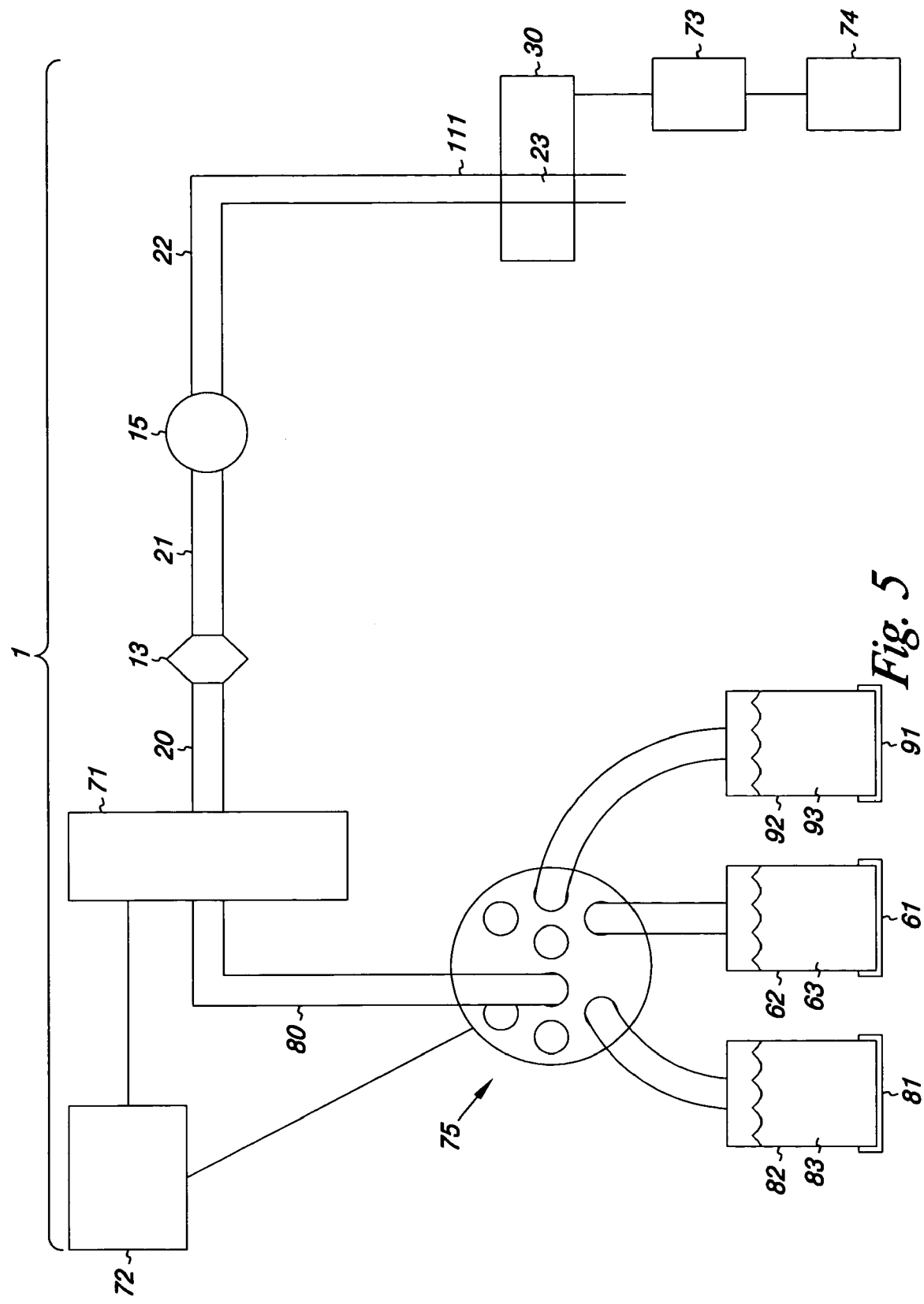
FIG. 5 shows another system of the invention for detecting bacteria in fluids.
Figure 6:
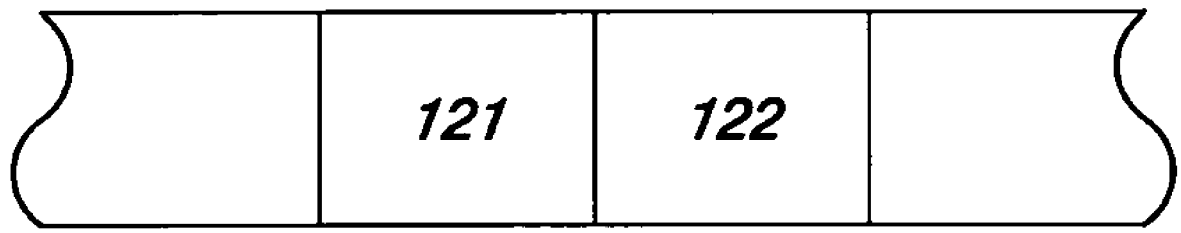
FIG. 6 shows tubing having two stacked zones of fluids.

It is also possible to have a system as shown in FIG. 5 with only one passageway emerging from the multiport selection device. Here, in some embodiments, if a wash solution containing a lysing agent and a luciferase solution are used, the solutions can be pumped through the passageways as stacked zones for mixing and analysis by sequential injection analysis (SIA) (11-15). Stacked fluid zones, such as 121 and 122 are produced in narrow bore tubing as shown in FIG. 6. One zone may contain bacterial ATP and another luciferase. The zones can be transported as adjacent unmixed zones into the assay chamber 22. Rapid bidirectional flow or unidirectional flow past a barrier such as a frit can mix the zones. Optionally, the stacked fluid zones can be separated by gas bubbles.

Upon mixing, the luciferase-catalyzed reaction produces light, which is detected by the detector. SIA is one mechanism for the luciferase to be contacted with the ATP in the assay chamber and in front of the detector, so that there is no delay between mixing of the ATP with the luciferase and flow of the assay solution into the detector. The light-producing luciferase reaction can decay rapidly, so it is advantageous to mix luciferase with the ATP in the assay chamber so there is no delay between mixing the ATP and the luciferase and detecting the reaction. This increases the sensitivity of the method. Other means of making the initial contact of ATP with luciferase in or immediately before the assay chamber are also possible. The luciferase solution can be mixed with the ATP-containing bacterial lysate fluid by connecting flows of the luciferase solution and the bacterial lysate fluid at a Y connection 111 immediately before the assay chamber as shown in FIG. 4. The luciferase can be immobilized in the assay chamber, e.g., on the walls of the assay chamber, so that the ATP of the bacterial lysate fluid initially contacts the luciferase in the assay chamber. Or a luciferase solution and an ATP-containing bacterial lysate fluid can be added separately to an assay chamber of the type shown in FIG. 1 and mixed in the assay chamber to form the ATP assay fluid.

Sequential injection analysis with narrow tubing has the advantage of minimizing the volumes of fluids consumed in the assay for bacteria and bacterial ATP. Both the volume of sample fluid and the volume of other reagents, such as luciferase, consumed can be minimized.

Some embodiments of the systems of the invention include a device for concentrating intact bacterial cells in fluid communication between the device for separating intact eukaryotic cells from intact bacterial cells and the assay chamber. The device for concentrating intact bacterial cells can involve, for instance, a support surface that binds bacterial cells or a filter that blocks passage of bacterial cells. Such an embodiment is shown in FIG. 4, where device 15 includes a bacteria-binding support surface.

ome embodiments of the invention include (d) a holding means for receiving a fluid sample reservoir in fluid communication with the device for separating intact eukaryotic cells from intact bacterial cells; (e) a pump functionally coupled to the fluid sample reservoir, the device for separating intact eukaryotic cells from intact bacterial cells (separation device), and the assay chamber, to pump fluid from the fluid-sample reservoir to the separation device, and from the separation device to the assay chamber; (f) a holding means for receiving a wash solution reservoir; and (g) a multiport selection valve in fluid communication with the device for separating intact eukaryotic cells from intact bacterial cells, the assay chamber, the fluid sample reservoir, and the wash solution reservoir, the multiport selection valve adapted for transmitting fluid from the fluid sample reservoir in one position and from the wash solution reservoir in another position.

In some embodiments, a processor is operably coupled to the pump and the multiport selection valve and programmed to deliver a predetermined volume of fluid from the fluid sample reservoir to the separation device, from the separation device to the assay chamber, and from the wash solution reservoir to the assay chamber.

One embodiment of the invention provides a system for detecting bacteria in a fluid sample that includes: (a) a holding means for receiving a support surface that binds intact bacterial cells in a fluid sample; (b) a fluid-tight material forming an assay chamber adapted to receive fluid flow from the support surface that binds intact bacterial cells in a fluid sample; and (c) a light detector functionally linked to the assay chamber to detect light emitted in the assay chamber.

In particular embodiments, the system includes in the holding means (a) the support surface that binds intact bacterial cells.

In a particular embodiment, the support surface does not bind ATP. This has the advantage that ATP present before the bacteria are lysed (i.e., potentially non-bacterial ATP) is separated from the intact bacteria and therefore separated from the bacterial ATP released when the bacteria are lysed.

In another particular embodiment, the support surface does not bind intact eukaryotic cells that may be present in the fluid sample.

In other embodiments, the support surface does bind intact eukaryotic cells. Contamination by eukaryotic ATP in these embodiments can be avoided by selectively lysing the eukaryotic cells before or after the fluid sample is contacted with the support surface, or otherwise removing the eukaryotic cells, e.g., by filtration, before or after the fluid sample is contacted with the support surface.

The invention will now be illustrated by the following non-limiting example.

EXAMPLE

Example 1

The assay procedure used was as follows.

1. A 1.0 ml platelet concentrate sample was pumped bidirectionally over a 40 microliter packed bead column of GenPoint BUG TRAP C-version beads (GenPoint, Oslo, Norway) for 60 seconds.

2. The column was flushed with 250 microliters of wash buffer, which was Hank's balanced salt solution (0.185 g/l $CaCl_2$, 0.2 g/l $MgSO_4$, 0.4 g/l KCl, 0.06 g/l $KH_2PO_4$, 8 g/l NaCl, 0.048 g/l $Na_2HPO_4$, 1.5 g/l dextrose anhydrous, 15.7 g/l dextrose monohydrate, 4.77 g/l HEPES, 1.365 g/l $NaH_2PO_4$).

3. Forty microliters of 0.1% trichloroacetic acid in water heated to 60° C. was bidirectionally passed over the column for 10 seconds to create a bacterial lysate fluid.

4. A luciferin-luciferase solution (10 microliters, containing 0.2 μg luciferase, 2 μg luciferin, in 50 mM sodium phosphate pH 7.5) was mixed with the bacterial lysate fluid by sequential injection analysis and mixing of the fluid zones (Global FIA, Fox Island, Wash.) to form an ATP assay fluid that was passed in front of a luminescence detector (photon counter, from Electron Tubes, England) to detect the burst of light.

One platelet concentrate bag was divided into four samples, each contained in a PL732 bag. Each bag was inoculated with 10 CFU/ml of *Escherichia coli, Pseudomonas aeruginosa, Staphylococcus aureus*, or *Serratia marcescens*. Four control bags were not inoculated with bacteria. After 36 hours at room temperature, 5 ml from each bag was transferred to BACT/ALERT culture bottles for automated culture system bacterial load detection. Using the BACT/ALERT, 5 ml of each sample was inoculated into standard aerobic, standard anaerobic, activated charcoal aerobic, and anaerobic bottles.

A 1.0 ml sample of each bag was tested as described above for bacterial ATP.

The results are shown in Table 1.

TABLE 1

| Strain | Inoculum (cfu/ml) | Time (hours) | BacT (cfu/ml) | Relative Light Units |
|---|---|---|---|---|
| E. coli | 10 | 36 | 517 | 1,476,200 |
| Pseudomonas | 10 | 36 | 772 | 1,807,426 |
| Staphylococcus | 10 | 36 | 415 | 1,267,845 |
| Serratia | 10 | 36 | 546 | 1,296,966 |
| E. coli | 0 | Post collection | Not detectable | 650 |
| Pseudomonas | 0 | Post collection | Not detectable | 713 |
| Staphylococcus | 0 | Post collection | Not detectable | 953 |
| Serratia | 0 | Post collection | Not detectable | 733 |

8. Nilsson L E et al. 1989. *J. Bioluminescence and Chemiluminescence* 3:101-104.

9. Stanley P E 1989. *J. Bioluminescence and Chemiluminescence* 4:375-380.

10. Lundin A, Thore A. 1975. *Applied Microbiology* 30:713-721.

11. Ruzicka J, Hansen E H. 1981. *Flow Injection Analysis*. J. Wiley and Sons.

12. Karlberg B, Pacey G E. 1989. *Flow Injection Analysis: A Practical Guide*. Elsevier.

13. Valcarcel M and Luque De Castro M D, *Flow-Injection Analysis. Principles and Applications*. John Wiley & Sons, New York.

14. U.S. Pat. No. 6,613,579.

15. U.S. Pat. No. 6,716,391.

16. Lemasters J J, Hackenbrock C R. 1979. *Meth. Enzymol.* 56:530-544.

17. Higashi T, et al. 1985. *Thrombosis and Haemostasis* 53:65-69.

All patents, patent documents, and other references cited are hereby incorporated by reference.

---

SEQUENCE LISTING

<160> NUMBER OF SEQ ID NOS: 1

<210> SEQ ID NO 1
<211> LENGTH: 7
<212> TYPE: PRT
<213> ORGANISM: Artificial
<220> FEATURE:
<223> OTHER INFORMATION: Bacteria-binding peptide

<400> SEQUENCE: 1

Phe His Arg Arg Ile Lys Ala
1               5

---

REFERENCES

1. Epstein J S, Williams A E, Biswas R, Vostal J. *FDA Update at the AABB Annual Meeting Oct.* 15, 2001.
2. Morrow J F, Braine H G, Kickler T S, Ness P M, Dick J D, Fuller A K. Septic reactions to platelet transfusions. A persistent problem. *JAMA*. 1991; 266(4):555-558.
3. Barrett B B, Andersen J W, Anderson K C. Strategies for the avoidance of bacterial contamination of blood components. *Transfusion*. March 1993; 33(3):228-233.
4. Dumont L. *Bacterial Contamination of Platelet Components*. Lakewood: COBE BCT Inc.; 1996.
5. Mitchell K-M T, Brecher M E. 1999. *Transfusion Medicine Reviews* 13:132-144.
6. Chaney R., et al. 1999. *Transfusion Medicine* 9:177-188.
7. Hanna B A. 1986. *Methods in Enzymology* 133:22-27.

What is claimed is:

1. A method of detecting bacteria in a fluid sample suspected of containing bacteria comprising:
    separating intact eukaryotic cells from suspected intact bacterial cells that may be present in the fluid sample, wherein said separating comprises
        filtering the eukaryotic cells using a filter that blocks the eukaryotic cells and allows bacterial cells that may be present to pass through, to generate a filtered fluid sample that may contain bacterial cells, and
        contacting the filtered fluid sample with a support surface that binds bacteria that may be present in the sample;
    lysing bacterial cells that may be present bound to said support surface to release bacterial ATP into a fluid to generate a bacterial lysate fluid;
    contacting bacterial ATP that may be present in the bacterial lysate fluid with an ATP-consuming enzyme that catalyzes a reaction in an ATP assay fluid; and monitoring the enzyme-catalyzed reaction in the ATP assay fluid;

wherein the fluid sample is a blood product for transfusion into a mammal;

wherein the method detects 10,000 bacterial colony forming units per ml or less of each of the following species of bacteria: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes,* and *Streptococcus viridans.*

2. The method of claim 1 wherein the intact eukaryotic cells include platelets.

3. The method of claim 1 wherein the support surface comprises glass, fibronectin, laminin, collagen, Arg-Gly-Asp oligopeptide, or Phe-His-Arg-Arg-Ile-Lys-Ala (SEQ ID NO:1) oligopeptide.

4. The method of claim 1 wherein the support surface does not bind the eukaryotic cells.

5. The method of claim 1 wherein the suspected bacterial cells are lysed while bound to the support surface to release bacterial ATP into a fluid to generate a bacterial lysate fluid.

6. The method of claim 1 further comprising eluting the suspected bacterial cells from the support surface into an elution fluid before the step of lysing the bacterial cells.

7. A method of detecting bacteria in a fluid sample suspected of containing bacteria comprising:

separating intact eukaryotic cells from suspected intact bacterial cells that may be present in the fluid sample, wherein the step of separating intact eukaryotic cells from bacterial cells comprises contacting the fluid sample with a support surface that binds the bacterial cells and does not bind the eukaryotic cells;

lysing bacterial cells that may be present bound to said support surface to release bacterial ATP into a fluid to generate a bacterial lysate fluid;

contacting bacterial ATP that may be present in the bacterial lysate fluid with an ATP-consuming enzyme that catalyzes a reaction in an ATP assay fluid; and monitoring the enzyme-catalyzed reaction in the ATP assay fluid;

wherein the fluid sample is a blood product for transfusion into a mammal;

wherein the method detects 10,000 bacterial colony forming units per ml or less of each of the following species of bacteria: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes,* and *Streptococcus viridans.*

8. The method of claim 7 wherein the support surface comprises polycations.

9. The method of claim 7 wherein the step of separating intact eukaryotic cells from intact bacterial cells that may be present in the fluid sample further comprises before the step of contacting the fluid sample with a support surface that binds the bacteria:

filtering the eukaryotic cells from the fluid sample using a filter that blocks the eukaryotic cells and allows the bacterial cells to pass through.

10. The method of claim 7 wherein the bacterial cells are lysed while bound to the support surface to release bacterial ATP into a fluid to generate a bacterial lysate fluid.

11. The method of claim 7 further comprising eluting the bacterial cells from the support surface into an elution fluid before the step of lysing the bacterial cells.

12. The method of claim 7 wherein the step of monitoring the enzyme-catalyzed reaction comprises monitoring a product produced by the reaction.

13. The method of claim 12 wherein the product is light.

14. The method of claim 13 wherein the enzyme is luciferase, the method further comprising contacting the bacterial ATP and luciferase with luciferin.

15. The method of claim 7 wherein the blood product is platelet concentrate.

16. The method of claim 7 wherein the blood product is whole blood, serum, plasma, bone marrow stem cell concentrate, or erythrocyte concentrate.

17. A method of detecting bacteria in a fluid sample suspected of containing bacteria comprising:

separating intact eukaryotic cells from suspected intact bacterial cells that may be present in the fluid sample; wherein said separating comprises filtering the eukaryotic cells using a filter that blocks the eukaryotic cells and allows bacterial cells that may be present to pass through, to generate a filtered fluid sample that may contain bacterial cells, and concentrating suspected intact bacterial cells in the filtered fluid sample by passing the filtered fluid sample through a second filter that blocks passage of bacterial cells;

lysing bacterial cells that may be present and blocked by the second filter to release bacterial ATP into a fluid to generate a bacterial lysate fluid;

contacting bacterial ATP that may be present in the bacterial lysate fluid with an ATP-consuming enzyme that catalyzes a reaction in an ATP assay fluid; and monitoring the enzyme-catalyzed reaction in the ATP assay fluid;

wherein the fluid sample is a blood product for transfusion into a mammal;

wherein the method detects 10,000 bacterial colony forming units per ml or less of each of the following species of bacteria: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes,* and *Streptococcus viridans;* wherein the volume of the ATP assay fluid is smaller than the volume of the fluid sample.

18. A method of detecting bacteria in a fluid sample suspected of containing bacteria comprising:

separating intact eukaryotic cells from suspected intact bacterial cells that may be present in the fluid sample, wherein said separating comprises filtering the eukaryotic cells using a filter that blocks the eukaryotic cells and allows bacterial cells that may be present to pass through, to generate a filtered fluid sample that may contain bacterial cells, and contacting the filtered fluid sample with a support surface that binds bacteria that may be present in the sample;

lysing bacterial cells that may be present and bound by said support surface to release bacterial ATP into a fluid to generate a bacterial lysate fluid;

contacting bacterial ATP that may be present in the bacterial lysate fluid with an ATP-consuming enzyme that catalyzes a reaction in an ATP assay fluid; and monitoring the enzyme-catalyzed reaction in the ATP assay fluid;

wherein the fluid sample is a blood product for transfusion into a mammal;

wherein the method detects 10,000 bacterial colony forming units per ml or less of each of the following species of bacteria: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans* wherein said support surface binds said species of bacteria; and wherein the volume of the ATP assay fluid is smaller than the volume of the fluid sample.

19. A method of detecting bacteria in a fluid sample suspected of containing bacteria comprising:

separating intact eukaryotic cells from suspected intact bacterial cells that may be present in the fluid sample, wherein said separating comprises contacting the fluid sample with a support surface that binds the bacterial cells that may be present in the fluid sample and does not bind eukaryotic cells;

lysing bacterial cells that may be present and bound by the support surface to release bacterial ATP into a fluid to generate a bacterial lysate fluid;

contacting the bacterial ATP that may be present in the bacterial lysate fluid with an ATP-consuming enzyme that catalyzes a reaction in an ATP assay fluid; and monitoring the enzyme-catalyzed reaction in the ATP assay fluid;

wherein the fluid sample is a blood product for transfusion into a mammal;

wherein the method detects 10,000 bacterial colony forming units per ml or less of each of the following species of bacteria: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans;* wherein the support surface binds said species of bacteria;

wherein the volume of the ATP assay fluid is smaller than the volume of the fluid sample.

20. The method of claim 17 wherein the method detects at least 3 bacterial genera at a level of 100 bacterial colony-forming units per ml of the fluid sample.

21. The method of claim 18 wherein the method detects at least 3 bacterial genera at a level of 100 bacterial colony-forming units per ml of the fluid sample.

22. The method of claim 19 wherein the method detects at least 3 bacterial genera at a level of 100 bacterial colony-forming units per ml of the fluid sample.

23. The method of claim 17 wherein the blood product is whole blood.

24. The method of claim 17 wherein the blood product is platelet concentrate.

25. The method of claim 17 wherein the step of monitoring the enzyme-catalyzed reaction comprises monitoring a product produced by the reaction, the product is light, the enzyme is luciferase, and the method further comprises contacting the bacterial ATP and luciferase with luciferin.

* * * * *